United States Patent [19]

Rogers et al.

[11] 4,205,002
[45] May 27, 1980

[54] ANTIBACTERIAL COMPOUNDS

[75] Inventors: Norman H. Rogers, Rudgwick; Peter J. O'Hanlon, Redhill, both of England

[73] Assignee: Beecham Group Limited, England

[21] Appl. No.: 955,196

[22] Filed: Oct. 27, 1978

[30] Foreign Application Priority Data

Nov. 1, 1977 [GB] United Kingdom ............... 45305/77

[51] Int. Cl.² .................... C07D 309/06; A61K 31/35
[52] U.S. Cl. .............................. 260/345.8 R; 424/283; 435/125; 435/876
[58] Field of Search ................... 260/345.7 R, 345.8 R

[56] References Cited

U.S. PATENT DOCUMENTS

| | | | |
|---|---|---|---|
| 4,071,536 | 1/1978 | Barrow et al. | 260/345.8 R |
| 4,102,901 | 7/1978 | Luk et al. | 260/345.8 R |
| 4,102,904 | 7/1978 | Luk et al. | 260/345.8 R |

FOREIGN PATENT DOCUMENTS 1395907 5/1975 United Kingdom ............ 260/345.8 R

*Primary Examiner*—Nicky Chan
*Attorney, Agent, or Firm*—Jacobs & Jacobs

[57] ABSTRACT

A compound of formula (II), named pseudomonic acid C or a salt or ester thereof:

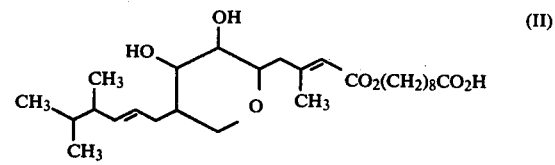

(II)

has antibacterial and anti-mycoplasma activity, and can be produced either by fermentation of *Pseudomonas fluorescens*, or by de-oxygenation of pseudomonic acid A, the compound having a epoxide in place of the double bond. The compounds are therefore useful in the treatment of human and veterinary bacterial and mycoplasma-induced infections.

6 Claims, No Drawings

ANTIBACTERIAL COMPOUNDS

This invention relates to antibacterial compounds and in particular to a novel antibacterial compound produced by the bacterium *Pseudomonas fluorescens*, together with salts and esters of the compound.

British Pat. No. 1,395,907 describes and claims a process for the isolation of antibacterial compounds from the bacterium *Pseudomonas fluorescens*, one such compound being called pseudomonic acid of formula (I)

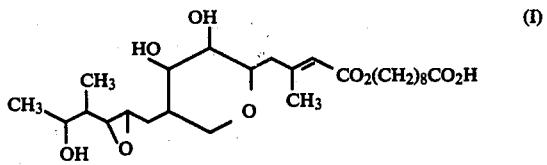

which will be referred to herein as "pseudomonic acid A".

It has now been found that a further antibacterial compound can be isolated from *Pseudomonas fluorescens* and this compound can also be prepared from pseudomonic acid A.

Accordingly the present invention provides a compound of formula (II) or a pharmaceutically acceptable salt or ester thereof:

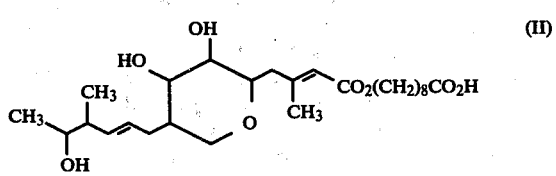

The compound (II) will be referred to herein as "pseudomonic acid C". It is believed that the compound has the absolute steriochemistry as shown in formula (III)

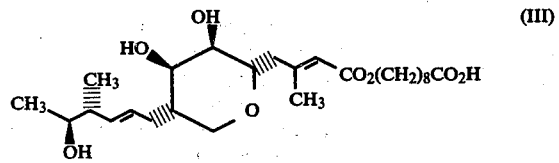

both double bonds being in the trans—or E configuration.

Suitable non-toxic salts of pseudomonic acid C include metal salts, e.g. aluminium, alkali metal salts such as sodium or potassium, alkaline earth metal salts such as calcium or magnesium, and ammonium or substituted ammonium salts for example those with lower alkylamino such as triethylamine, hydroxy-lower alkylamines such as 2-hydroxyethylamine, bis-(2-hydroxethyl)-amine or tri-(2-hydroxyethyl)-amine, cycloalkylamines such as bicyclohexylamine, or with procaine, dibenzylamine, N,N-dibenzylethylene-diamine, 1-ephenamine, N-ethylpiperidine, N-benzyl-β-phenethylamine, dehydroabietylamine, N,N'-bis-dehydroabietylethylenediamine, or bases of the pyridine type such as pyridine, collidine or quinoline.

Preferred salts are alkali metal salts. Suitable esters include:

(a) $C_{1-20}$ alkyl, $C_{2-8}$ alkenyl or $C_{2-8}$ alkynyl each of which may be optionally substituted by $C_{3-7}$ cycloalkyl, halogen, carboxy, $C_{1-6}$ alkoxycarbonyl, carbamoyl, aryl, heterocyclyl, hydroxy, $C_{1-16}$ alkanoyloxy, amino, mono- and di-$(C_{1-6})$ alkylamino.

(b) $C_{3-7}$ cycloalkyl optionally substituted with $C_{1-6}$ alkyl;

(c) aryl;

(d) heterocyclyl.

The term 'aryl' includes phenyl, and naphthyl optionally substituted with up to five halogen, $C_{1-6}$ alkyl, $C_{1-6}$ alkoxy, halo($C_{1-6}$)alkyl, hydroxy, amino, carboxy, $C_{1-6}$ alkoxycarbonyl, or $C_{1-6}$ alkoxycarbonyl $(C_{1-6})$alkyl groups.

The term 'heterocyclyl' includes single or fused rings comprising up to four hetero atoms in the ring selected from oxygen, nitrogen sulphur and optionally substituted with up to three halogen, $C_{1-6}$ alkyl, $C_{1-6}$ alkoxy, halo($C_{1-6}$)alkyl, hydroxy, amino, carboxy, $C_{1-6}$ alkoxycarbonyl, $C_{1-6}$ alkoxy-carbonyl($C_{1-6}$)alkyl, aryl or oxo groups.

One class of ester groups comprise alkyl, aryl, and aralkyl groups, any of which may be substituted with a hydroxy, amino or halogen group. For example the ester group may be a $C_{1-6}$ alkyl group in particular, methyl, ethyl, n or iso-propyl, n, sec-, iso or tert-butyl; a halo-($C_{1-6}$)-alkyl group such as trifluoromethyl, 2,2,2-trichloroethyl; an aminoalkyl group such as aminomethyl, 2-aminoethyl; hydroxymethyl, hydroxyethyl; phenyl; substituted phenyl, or a benzyl group.

Preferred esters are $C_{1-6}$ alkyl esters.

Pseudomonic acid C, its salts and esters have antibacterial activity. They have particularly high activity against *Haemphilus influenzae*, *Neisseria gonorrhoeae* and *Mycoplosma sp*, and are therefore of value in the treatment of respiratory and venereal diseases, and of mycoplasma-induced human and veterinary diseases. Furthermore, the compounds of this invention have the advantage over pseudomonic acid A of being stable to acidic conditions, and more stable to alkaline conditions.

In humans the infections which pseudomonic acid C its salts and esters may be particularly useful against include venereal disease. Because it is not a β-lactam antibiotic it is effective against β-lactamase-producing strains of *N. gonorrhoeae*, against which standard treatments such as penicillin and cephalosporin antibiotics would not be useful. Pseudomonic acid C may also be effective in the treatment of respiratory infections such as chronic bronchitis, and bacterial meningitis; nonspecific urethritis and pneumonia. In animals it may be employed generally as a growth promoter, or for the treatment of mastitis in cattle and for treatment of mycoplasma infections in animals such as turkeys, chickens and pigs.

This invention also provides a pharmaceutical or veterinary composition which comprises pseudomonic acid C, or a salt or ester thereof together with a pharmaceutically or veterinary acceptable carrier or excipient.

The compositions may be formulated for administration by any route, and would depend on the disease being treated. The compositions may be in the form of tablets, capsules, powders, granules, lozenges, or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats, emulsifying agents, for example lecithin, sorbitan monooleate, or acacia; non aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired convention flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability the composition can be frozen after filling into the vial and water removed under vacuum. The dry lypophilized powder is then sealed in the vial. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10-60% by weight, of the active material, depending on the method of administration. Where the compositions comprise dosage units, each unit will preferably contain from 50-500 mg., of the active ingredient. The dosage as employed for adult human treatment will preferably range from 100 mg to 3 g., per day, for instance 250 mg-2 g., per day, depending on the route and frequency of administration.

Alternatively pseudomonic acid C or a salt or ester may be administered as part of the total dietary intake. In this case the amount of compound employed may be less than 1% by weight of the diet and in preferably no more than 0.5% by weight. The diet for animals may consist of normal foodstuffs to which the compound may be added or it may be added to a premix.

The present invention also provides a process for the preparation of pseudomonic acid C or a salt or ester thereof which process comprises reacting pseudomonic acid A or a salt or ester thereof with a reagent which converts an epoxide to an olefin; and optionally carrying out one of the following steps:
(i) forming a salt of the pseudomonic acid C produced;
(ii) esterifying the pseudomonic acid C or salt thereof to produce an ester of pseudomonic acid C; or
(iii) hydrolysing an ester of pseudomonic acid C.

A number of reagents for converting an epoxide to an olefin are known in the literature, and the particular reagent of choice for the process of the present invention is a matter of trial and error. Some such reagents are more suitable than others for this purpose. Some generally applicable methods are as follows:
(a) Potassium selenocyanate in methanol/water; (see JCS Chem. Comm., 1975, 1216; JCS 1949, 278)
(b) Lower valent tungsten halides; for example $WCl_6$/butyl lithium (see J. Amer. Chem. Soc. 1972,94,6538)
(c) $Ph_3P=Se$/trifluroacetic acid; (see JCS Chem. Comm. 1973, 253)
(d) Trifluoroacetyl iodide/sodium iodide; (see J. Org. Chem., 1978,43,1841).

Other methods are described in the following references:
J. Amer. Chem. Soc., 1973, 95, 2697.
Tet. Letts (17) 1976, 1395.
Ber. 1955, 88, 1654.
J. Org. Chem., 1958, 22, 1118.

It has been found that one convenient method is the use of potassium selenocyanate.

Suitable solvents for use with potassium selenocyanate include mixtures of water with alkanols, in particular $C_1$-$C_{20}$ alkanols. It has been found that higher yields of the compound of formula (II) are achieved if an alcohol is employed with a large, in particular branched or cyclic, alkyl group. Specific alcohols include isohexyl alcohol, tert-amyl alcohol and cyclohexyl alcohol. The reaction is generally performed at elevated temperatures, suitably at about the boiling point of the solvent employed. The time for which the reaction is performed depends on the temperature of the reaction, and therefore on the solvent. Generally a time of from 2-9 days is suitable.

Another suitable method for converting the epoxide of pseudomonic acid A, or a salt or ester thereof into an olefin, comprises treatment with trifluoroacetyl iodide and sodium iodide. The trifluoroacetyl iodide may be prepared in situ from trifluoroacetic anhydride. The reaction is suitably conducted at ambient temperature for from about 10 to 36 hours, suitably about 24 hours.

When the free acid or salt of pseudomonic acid C is required it may be convenient to employ an ester of pseudomonic acid A for the above process, which ester is a carboxyl-protecting group. Suitable carboxyl-protecting groups would depend on the reaction conditions for de-epoxidation and include the 2,2,2-trichloro-ethyl ester, (which may be removed with zinc in a lower alcohol, especially methanol) phenyl, pentachlorophenyl, benzyl, and t-butyl ester groups. Other suitable carboxyl-protecting are silyl groups. In this case the carboxylic acid is reacted with a silylating agent such as a halosilane or a silazane. A preferred silylating agent is N,O-bis(trimethylsilyl) acetamide, which produces the trimethyl-silyl derivative of the acid.

Prior to the above process of this invention, it may be desirable to protect the hydroxyl groups in pseudomonic acid A or its salt or ester. Although the reaction is possible without hydroxyl protection, in some cases higher yields of the pseudomonic acid C derivative could be formed if the hydroxyl groups were protected. Such protecting groups must be removable under suitably mild conditions and suitable groups include silyl groups produced from a silylating agent as discussed above. Particularly suitable hydroxyl-protecting groups include tri-methylsilyl, t-butyldimethylsilyl, methylthiomethyl. A preferred hydroxyl-protecting group is trimethylsilyl, as it is readily removed on completion of the reaction. Alternatively, for some de-epoxidation reactions it is possible to protect the hydroxyl groups with other ester radicals which may be removed by chemical or enzymatic means. Examples include p-nitrobenzoate, methoxyacetate, phenoxyacetate, trifluoroacetate, each of which may be removed under mild basic conditions such as aqueous ammonia; or potassium carbonate in aqueous methanol.

It is also possible to protect the glycol moiety in pseudomonic acid A, and suitable reagents for forming such a hydroxyl-protecting group include compounds of formula (IV).

wherein $R^1$ is hydrogen or a $C_{1-6}$ alkyl group and $R^2$, $R^3$ and $R^4$ independently represent a $C_{1-6}$ alkyl group.

The group $R^1$ may be for example hydrogen, methyl, ethyl, n- or iso-propyl. Most suitably, $R^1$ represents hydrogen so that the compound of formula (IV) is a trialkyl orthoformate.

Groups $R^2$, $R^3$, and $R^4$ may be for example, methyl, ethyl, n- or iso-propyl, n-, iso-, sec- or tert-butyl. Preferably $R^2$, $R^3$, and $R^4$ are all the same and each represents a methyl group.

Other glycol protecting groups include those wherein the glycol moiety is converted to the structure:

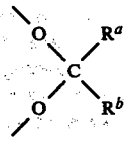

where $R^a$ and $R^b$ are hydrogen, $C_{1-6}$ alkyl, or phenyl. Preferably $R^a$ and $R^b$ are both methyl, i.e. the group is the isopropylidene group. This group may be introduced onto pseudomonic acid A or its salt or ester by reaction with 2,2-dimethoxypropane, and removed by treatment with acetic acid.

The hydroxy-protecting group may be removed by a conventional method for the particular hydroxyl-protecting group.

It may be such that it can be removed directly or alternatively, it may be converted into a different protecting group which is then removable under different conditions. This latter approach may be employed when a glycol protecting group derived from a compound (IV) is used; it is converted by acid to the group $—OCOR^1$ which is then removed.

When an ester of pseudomonic acid C is required, the esterification step, step (ii) above may be performed by any conventional method, for example by reaction of the acid, or a salt thereof:

(a) with the appropriate halide, sulphate or alkanesulphonate of the alcohol in the presence of a solvent such as acetone, dimethylsulphide or dimethylsulphoxide and calcium, or potassium carbonate or with the halide in the presence of hexamethyl phosphoramide; or (b) by phase transfer catalysis methods with the halide and/or sulphate of the alcohol in aqueous and/or organic solution in the presence of a quaternary ammonium salt such as tetrabutyl ammonium bisulphate or halide, or benxyltrimethyl-ammonium halide; or (c) with a diazoalkane.

The hydrolysis of an ester of pseudomonic acid C (step (iii) above) may be chemical hydrolysis, for example by selective alkaline hydrolysis; or enzymic hydrolysis, for example by the use of Bakers' Yeast.

Also included within the scope of the present invention is a process for the preparation of pseudomonic acid C or a salt or ester thereof which comprises growing *Pseudomonas fluorescens* under aerobic conditions on or in a culture medium containing inorganic salts and sources of asimilable carbon and nitrogen until the culture medium exhibits at least detectable antibacterial activity, acidifying the culture medium; extracting with an organic solvent for the active materials dissolved in the culture medium, and thereafter either:

(a) separating pseudomonic acid C or a salt thereof from any other active materials and optionally thereafter esterifying the separated acid; or (b) esterifying the active materials, separating an ester of pseudomonic acid C from esters of any other active materials and optionally thereafter hydrolysing the separated ester to form pseudomonic acid C or a salt thereof.

In the above process, the cultivation step where *Pseudomonas fluorescens* is grown is conventional. Any strain of this organism may to our knowledge be employed; one suitable public strain being *Pseudomonas fluorescens* NCIB 10586. (NCIB = National Collection of Industrial Bacteria).

After the fermentation is completed, the active materials, including pseudomonic acid C, are extracted from the acidified aqueous culture medium into a suitable solvent.

Preferably, the extraction procedure comprises extraction of the culture medium, after acidification, with an organic solvent; re-extraction of the organic extract with aqueous alkaline buffer solution; and finally re-extraction of the latter, after acidification, with organic solvent. Suitable solvents can be found by trial and error; examples include iso-butylmethyl ketone (IBMK), chloroform and preferably ethyl acetate.

The pseudomonic acid C may then be separated from other active materials produced in the fermentation, either directly (step (a) above) or by esterifying the mixture and separating the ester of pseudomonic acid C (step (b) above). When *Pseudomonas fluorescens* NCIB 10586 is employed as the bacterium, the major material which is produced in addition to pseudomonic acid C is pseudomonic acid A. If this latter material is present in substantial quantities it is preferable to remove the majority by crystallisation of pseudomonic acid A, optionally with seeding, from a suitable solvent for example diethyl ether.

If alternative (a) is carried out pseudomonic acid C may be separated directly by chromatography from the remaining mixture, either as the free acid itself or as a slat thereof. On chromatography on silica gel, pseudomonic acid C is eluted slightly before pseudomonic acid A and the fractions can be identified accordingly.

The separated pseudomonic acid C or a salt thereof may be esterified by any of the methods described earlier in this specification.

If alternative (b) above is carried out the mixture of active materials is first esterified, preferably after removing the majority of the pseudomonic acid A by crystallisation. Again any of the above described methods of esterification may be employed. It is convenient to form $C_{1-6}$ alkyl esters of the components in the mixture, preferably methyl esters.

The resultant mixture of esters may then be subjected to chromatography and the desired ester of pseudomonic acid C thereby separated. If the free acid or salt is required they may be produced by chemical or enzymatic hydrolysis of the separated ester.

The invention is illustrated in the following Examples.

EXAMPLE 1

Methyl 10,11-Deoxypseudomonate A (methyl pseudomonate C) from methyl pseudomonate A A solution of methyl pseudomonate A (1.03 g; 2 m.mole) and potassium selenocyanate (0.846 g; 6 m.mole) in methanol-water 9:1 (30 ml) was heated under reflux for 7 days. The black precipitate of selenium was filtered off and the filtrate evaporated to an oil. The latter was partitioned between ethyl acetate and water and the organic phase separated, washed with sodium bicarbonate, brine, dried (MgSO$_4$) and evaporated to an oil. Chromatography on silica gel H (type 60) using a gradient of chloroform to 4% methanol-chloroform afforded methyl 10,11-deoxypseudomonate as an oil (0.129 g), tlc in chloroform-methanol 9:1 showed one component at Rf=0.46 and a single peak by hplc, $\nu_{max}$ (CHCl$_3$) 3400, 2900, 2850, 1720, 1710, 1650, 1150 and 980 cm$^{-1}$, $\lambda_{max}$ (EtOH) 221 nm ($\epsilon$11,500), $\delta_H$(CDCl$_3$) 5.75 (1H, m, C2-H), 5.40 (2H, m, C10-H and C11-H), 4.05 (2H, t, C9'-CH$_2$) 3.65 (3H, s, CH$_3$O), 2.21 (3H, broad s, C15-CH$_3$), 1.21 (3H, d, C17-CH$_3$) and 1.00 (3H, d, C14-CH$_3$), $\delta_C$(CDCl$_3$, 174.3 (C1'), 166.8 (C1), 156.8 (C3), 134.5 and 129.4 (c10 and 11), 117.6 (C2), 74.8 (C5), 71.2 (C13), 70.4 (C7), 68.9 (C6), 64.8 (C16), 63.8 (C9'), 51.4 (CH$_3$O), 44.7 and 43.1 (C4 and 12), 42.0 (C8), 34.1 (C2'), 32.4 (C9), 29.1 (C4',5' and 6'), 28.7 (C8'), 26.0 (C7'), 24.9 (C3'), 20.4'C14), 19.1 (C15) and 16.6 (C17), m/e (relative intensity) 499 (100%, M$^+$+1 by C.I.)

EXAMPLE 2

Pseudomonic acid C by fermentation (a) fermentation

*Pseudomonas fluorescens*, strain NCIB 10586 was cultured on an agar slope and flooded with sterile water. A sample was added to the following seed stage medium:

Oxoid yeast extract: 2% (w/v)
Glucose: 0.11
Disodium hydrogen orthophosphate: 0.26
Potassium dyhydrogen orthophosphate: 0.24
This was grown at 28° C. overnight and then used to inoculate the following production stage medium:
Corn steep liquor: 0.3% (w/v)
Glucose: 2.0
Glycerol: 0.5
Ammonium sulphate: 0.2
Calcium carbonate: 0.4
Potassium dyhydrogen orthophosphate: 0.04
Disodium hydrogen orthophosphate: 0.065
Manganese chloride R H$_2$O: 0.0003
Potassium chloride: 0.05
Magnesium sulphate 7 H$_2$O: 0.0375
P2000 to minimise foaming.

The fermentation was carried out at 25° C. for 48 hours when production was essentially complete. After removing the cells by centrifugation the supernatant was partitioned into ethyl acetate at pH 3. The ethyl acetate solution was dried (MgSO$_4$) evaporated to low volume, ether added and pseudomonic acid A allowed to crystallise.

(b) Isolation of Pseudomonic acid C

The mother liquors from the above crystallization were evaporated to an oil and chromatographed on silica gel preparative 20×20 cm thin layer chromatography plates developed with chloroform:isopropanol:acetic acid (80:20:0.5). The band above pseudomonic acid A of Rf 0.65 was removed and re-chromatographed as before to give pseudomonic acid C. [Found: C, 64.0; H, 9.3%, C$_{26}$H$_{44}$O$_8$ requires C, 64.4; H, 9.2%], $\nu_{max}$ (CHCl$_3$) 3430 (broad, 1710, 1650, 1220 (broad), 1153, 1110, 1050, and 977 cm$^{-1}$, $\epsilon_{max}$(EtOH) 222 nm ($\epsilon$ 14,100) $\delta_H$(CDCl$_3$) 5.69 (1H, m C2-H, 5.4 (2H, m, C10-H), 4.65 (4H, broad), 4.01 (2H, t, C9'-CH$_2$), 2.15 (3H, s, C15-CH$_3$), 1.12 (3H, d, C17-CH$_3$; J=6 Hz), 0.96 (3H, d, C14-CH$_3$; J=8 Hz), $\delta_C$(CDCl$_3$) 178.1 (C1'), 166.9 (C1), 156.9 (C3), 134.5 and 129.5 (C10 and C11), 117.6 (C2), 74.9 (C5), 71.4 (C13), 70.4 (C7), 69.0 (C6), 64.9 (C16), 63.9 (C9'), 44.7 (C12), 43.0 (C4), 41.9 (C8), 34.0 (C2'), 32.4 (C9), 28.9 (C4', 5' and 6'), 28.6 (C8'), 25.9 (C7'), 24.7 (C3'), 20.4 (C14), 19.2 (C15), 16.7 (C17).

EXAMPLE 3

Isolation of Methyl Pseudomonate C

The residual oil from the mother liquors from Example 2(a) (ca 5 g) was dissolved in methanol (50 ml), diluted with water (50 ml) and the pH adjusted to 7 with aqueous sodium hydroxide. After evaporation to dryness a solution of the residue in dimethylformamide (50 ml), hexamethylphosphoramide (5 drops) and methyl iodide (5 ml) was stirred overnight at room temperature. The solution was evaporated to dryness and the residue partitioned between ethyl acetate (50 ml) and water (20 ml). The organic layer was washed with saturated brine, aqueous sodium bicarbonate, brine, dried (MgSO$_4$), and evaporated to an oil from which some methyl pseudomonic A crystallised. The residual oil was chromatographed twice on silica (20 g then 15 g, type 60) eluting with gradient of 0–4% methanol - chloroform. Fractions containing substantially pure methyl pseudomonate C (Rf 0.46 silica tlc, chloroform/methanol 9:1, methylpseudomonate A Rf 0.42) were combined and chromatographed on silica (4 g, type 60) using gradient of 0–3% methanol - chloroform (distilled from phosphorus pentoxide). Fractions containing pure methyl pseudomonate C (by tlc) were combined and evaporated to an oil (50 mgs) which was found to be spectroscropically and chromatographically identical to methyl 10,11-deoxypseudomonate A obtained in Example 1.

EXAMPLE 4

Pseudomonic Acid C from methyl pseudomonate C

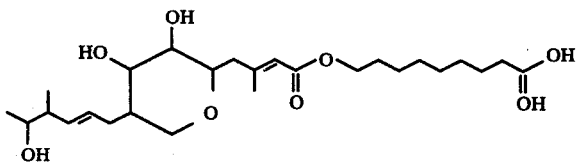

Methyl pseudomonate C (230 mgs) from Example 3 was dissolved in DMF (25 ml) and diluted with 0.05 M phosphate buffer (120 ml) then stirred with Bakers Yeast (6 g) overnight. The mixture was filtered, evaporated to dryness and the residue dissolved in ethyl acetate (50 ml) and water (50 ml). The organic layer was washed with water and combined aqueous layers adjusted to pH 3 (5 M HCl) and extracted several times with ethyl acetate. After drying the combined extracts were evaporated to yield an oil. Chromatography on silica gel H (type 60, 8 g) eluting with gradient 0 to 6% methanol - chloroform gave pseudomonic acid C (150 mgs, 67%) which was chromatographically and spectroscopically identical to material obtained in Example 2.

EXAMPLE 5

Methyl Pseudomonate C (Alternative procedure to Example 3)

Mother liquors (15 g) from Example 2 (a) were dissolved in acetone (150 ml), and stirred overnight with potassium carbonate (42 g) and methyl iodide (21 ml) at room temperature. The reaction mixture was filtered and the filtrate evaporated to dryness then taken up in ethyl acetate/water and worked up as in Example 3 to give methyl pseudomonate C.

The methyl ester may be hydrolysed as in Example 4.

EXAMPLE 6

Sodium Pseudomonate C (Sodium, 10,11-deoxypseudomonate A)

A solution of methyl pseudomonate C (0.330 g) in distilled tetra-hydrofuran (20 ml) and N/10 sodium hydroxide solution (20 ml) was stirred at room temperature for 2 hours. The tetrahydrofuran was removed in vacuo to give a turbid aqueous solution, which was washed with ether-ethyl acetate to remove unreacted ester. The aqueous layer was saturated with sodium chloride, layered with ethyl acetate and acidified with dilute hydrochloric acid to pH 1.5. The ethyl acetate layer was separated, washed with brine, dried (MgSO$_4$) and evaporated to dryness. The pseudomonic acid C obtained was suspended in water - tetrahydrofuran and N/10 sodium hydroxide solution added to pH 7.5. The resulting aqueous solution was evaporated to dryness in vacuo. The residue was dissolved in dry methanol (5 ml) filtered and excess dry ether added to the filtrate with stirring. The resulting white precipitate of sodium pseudomonate C was collected and dried in vacuo (0.153 g). The compound was homogeneous by thin layer chromatography and high pressure liquid chromatography, $[\alpha]_D^{20}$—0.94 (c 1.0, MeOH), $\lambda_{max}$ (KBr) 3400, 2800, 1700, 1640, 1560, 1230, 1150, 975 cm$^{-1}$, $\lambda_{max}$(EtOH) 221 nm ($\epsilon$ 13,300), $\epsilon_H$((CD$_3$)$_2$SO)) 5.7 (1H, m, vinylic-H), 5.3 (2H, m, —CH=CH—), 3.95 (2H, 5, C$\underline{H}_2$-9'), 2.08 (3H, s, vinylic —CH$_3$), 0.95 (3H, d, secondary —CH$_3$) and 0.88 (3H, d, secondary —CH$_3$).

EXAMPLE 7

Sodium Pseudomonate C

Methyl pseudomonate C (1 g) was dissolved in THF (50 ml)/water (50 ml) and the pH adjusted to 12 and maintained for 2½ hours. The solution was adjusted to pH7 and evaporated to dryness then redissolved in water (30 ml) and washed with ethylacetate. The aqueous fraction was then acidified to pH2 and extracted with ethyl acetate. After drying (MgSO$_4$) the combined extracts were evaporated in vacuo. The resultant oil (0.55 g) was treated with sodium bicarbonate (95 mgs, 1 eq) in water (20 ml)/methanol (20 ml) and evaporated to dryness. The sodium salt was dissolved in ethanol (minimum) and added dropwise to ether (300 ml) and the precipitate filtered off (0.58 g, 57%), $\lambda_{max}$ (KBr) 3380 (broad), 1700, 1642, 1560, 1225, 1150 and 973 cm$^{-1}$, $\lambda_{max}$ (EtOH) 222 nm ($\delta$ 13,700), $\epsilon_H$(CH$_3$OD) 1.07 (3H, d, J 7 Hz, C17-C$\underline{H}_3$), 1.18 (3H, d, J 7 Hz, C14-C$\underline{H}_3$), 1.44 (12H, m,-(CH$_2$)$_6$), 2.25 (3H, s, C15-C$\underline{H}_3$), 4.11 (2H, 5, C9-C$\underline{H}_2$), 5.5 (2H, m, H-10, H-11), 5.79 (1H, s, H-2), $\delta_c$ (CD$_3$OD) 183.0 (C1'), 168.4 (C1), 158.9 (C3), 135.7, 129.6 (C10, C11), 118,2 (C2), 76.2 (C5), 72.0 (C7), 71.5 (C13), 69.8 (C6), 65.6 (C16), 64.8 (C9'), 45.2 (C12), 44.0, 43.6 (C4, C8), 39.3 (C2'), 33.6 (C9), 30.7, 30.4, 30.3, 29.8, 27.7, 27.1 (C3'-C8'), 20.3 (C14). 19.4 (C15), 16.6 (C17) (Found: C, 59.4; H, 8.4; Na, 4.9.C$_{26}$H$_{43}$O$_8$Na.H$_2$O requires C, 59.5; H, 8.6; Na, 4.4%).

EXAMPLE 8

Pseudomonic acid C

Pseudomonic acid A (500 mgs) was dissolved in 2,2-dimethoxypropane (20 ml) and ethyl acetate (20 ml) then p-toluene sulphonic acid (few crystals) added. The solution was stirred for 1 hour then washed with brine and dried (MgSO$_4$). After evaporation of the solvent in vacuo, the residue was dissolved in water-methanol (1:1, 20 ml) and potassium bicarbonate (100 mgs, 1 eq) added. The solvents were removed in vacuo and potassium selenocyanate (432 mgs, 3 eq), tert-amyl alcohol-water (9:1, 15 ml) added and the reaction refluxed for 4 days. After filtering the solution was evaporated to dryness, water (20 ml) added and solution adjusted to pH2 (5 M-HCl) under a layer of ethyl acetate (20 ml). The organic layer was separated and the aqueous layer further extracted with ethyl acetate (3×20 ml). The combined extracts were dried (MgSO$_4$) and evaporated to an oil which was redissolved in 80% acetic acid (10 ml) and stirred at room temperature overnight. The solution was evaporated to dryness and the residual oil chromatographed on silica (10 g) eluting with 0 to 6% methanol-chloroforom. Fractions containing pure product (tlc) were combined and evaporated to give pseudomonic acid C (280 mgs, 58%).

EXAMPLE 9

Pseudomonic acid C

Pseudomonic acid A (500 mgs) was dissolved in 2,2-dimethyoxypropane (50 ml) and treated with p-toluene sulphonic acid (few crystals). After 1 hour the solution was diluted with ethyl acetate, washed with brine and dried (MgSO₄). The solution was evaporated in vacuo and the residue redissolved in water-methanol (1:1, 20 ml) and potassium bicarbonate (100 mgs, 1 eq) added. The solvents were removed in vacuo and potassium selenocyanate (432 mgs, 3 eq) and iso-hexylalcohol-water (9:1, 15 ml) added and reaction refluxed for 4 days. After filtering, the reaction mixture was diluted with ethyl acetate (20 ml) and extracted with aqueous sodium bicarbonate (3×20 ml). The aqueous extracts were combined and acidified with acetic acid under a layer of ethylacetate (20 ml). After stirring for ca. 1 hour the organic layer was separated and aqueous layer further extracted with ethylacetate (3×20 ml). The combined extracts were washed with brine, dried (MgSO₄) and evaporated to an oil. Chromatography of the oil on silica (5 g) gave pure pseudomonic acid C (215 mgs, 45%).

EXAMPLE 10

Methyl pseudomonate C

Methyl pseudomonate A (5.14 g), potassium selenocyanate (4.32 g) in iso-hexyl alcohol - water (9:1, 150 ml) were refluxed for 3 days. The reaction mixture was filtered then evaporated to dryness and dissolved in ethyl acetate (50 ml) - brine (50 ml). The organic layer was separated, washed with brine (50 ml) then dried (MgSO₄). After evaporation of the solvents in vacuo, the residue was chromatographed on silica (80 g) eluting with 0–4% methanol-chloroform. Pure fractions were combined and evaporated to an oil which on standing gave crystalline methyl pseudomonate C, mp. 47°–9° C. (2.57 g, 52%) (Found: C, 65.0; H, 9.5. $C_{27}H_{46}O_8$ requires C, 65.0; H, 9.3%).

EXAMPLE 11

Methyl pseudomonate C and pseudomonic acid C

Methyl pseudomonate A (514 mgs) was dissolved in 2,2-dimethoxypropane (20 ml) and a few crystals of p-toluene sulphonic acid added. The solution was stirred for ½ hour then ethyl acetate (20 ml) added and the solution washed with brine then dried (MgSO₄). After evaporation of the solvents, the acetonide was dissolved in tert-amyl alcohol-water (9:1, 15 ml), potassium selenocyanate (432 mgs) added and reaction refluxed for 5 days. The solution was filtered, evaporated to dryness and the residue dissolved in ethyl acetate (20 ml)-brine (20 ml). The organic layer was separated and the aqueous layer further extracted with ethyl acetate (3×20 ml). The combined extracts were dried (MgSO₄) and evaporated to dryness. The crude product contained two major components (tlc) which were separated by column chromatography on silica (10 g) eluting with 0–8% methanol-chloroform. The first fraction was identified as methyl 6,7-O-isopropylidene pseudomonate C (206 mgs, 38%), $\nu_{max}$ (CHCl₃) 3450, 1722, 1643 and 1220 cm⁻¹, $\delta_H$(CDCl₃) 0.98 (3H, d, J 7 Hz, C17-C$\underline{H}_3$), 1.13 (3H, d, J 7 Hz, C14-C$\underline{H}_3$), 1.33 (15H, m, (CH₂)₆, acetonide C$\underline{H}_3$), 1.48 (3H, s, acetonide C$\underline{H}_3$), 2.18 (3H, s, C15-C$\underline{H}_3$), 3.63 (3H, s, OC$\underline{H}_3$), 4.05 (2H), t, C9'-C$\underline{H}_2$), 5.45 (2H, m, $\underline{H}$-10, H-11), 5.73 (1H, s, $\underline{H}$-2), $\delta_c$(CDCl₃) 174.0 (C1'), 166.6 (C1), 156.2 (C3), 135.0, 128.9 (C10, C11), 117.8 (C2), 108.7 (>C<), 76.5 (C5), 76.7 (C7), 74.3 (C6), 71.0 (C13), 66.5 (C16), 63.7 (C9'), 51.3 (OCH₃), 44.6 (C12), 44.1 (C4), 37.9 (C8), 34.2 (C2'), 34.1 (C9), 29.1 (C4', 5', 6'), 28.8 (C8'), 28.3,

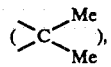

26.0 (C7'), 24.9 (C3'), 20.3 (C14), 19.1 (C15), 16.4 (C17), m/e (relative intensity) 523 (6%), 494 (19), 436 (22), 369 (30), 306 (22), 299 (20) (Found: 523.3263. M⁺-CH₃ requires 523.3257). The second fraction was identified as 6,7-O-isopropylidene pseudomonic acid C (130 mgs, 25%), $\nu_{max}$ (CHCl₃) 2300–3600 (broad), 1702, 1642, 1220, 1152 and 1052 cm⁻¹, $\delta_H$(CDCl₃) 0.98 (3H, d, J 7 Hz, C17-C$\underline{H}_3$), 1.14 (3H, d, J 7 Hz, C14-C$\underline{H}_3$), 1.33 (15H, m, (CH₂)₆, acetonide CH₃), 1.49 (3H, s, acetonide C$\underline{H}_3$), 2.18 (3H, s, C15-C$\underline{H}_3$), 4.06 (2H, t, C9'-C$\underline{H}_2$), 5.45 (2H, m, $\underline{H}$-10, $\underline{H}$-11), 5.73 (1H, s, $\underline{H}$-2), $\delta_c$(CDCl₃) 178.1 (C1'), 166.7 (C1), 156.1 (C3), 134.9, 129.0 (C10, C11), 117.8 (C2), 108.7 (>C<), 76.4 (C5), 75.6 (C7), 74.2 (C6), 71.2 (C13), 66.4 (C16), 63.8 (C9'), 44.4 (C12), 44.0 (C4), 36.8 (C8), 34.0 (C2'), 33.7 (C9), 29.0 (C4', 5', 6'), 28.7 (C8'), 28.3,

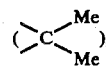

25.9 (C7'), 24.7 (C3'), 20.1 (C14), 19.0 (C15), 16.4 (C17), m/e (relative intensity) 509 (7%), 480 (10), 422 (10), 404 (8), 394 (10), 387 (7), 383 (8). (Found: 509.3110. M⁺-CH₃ requires 509.3108). The acetonides were quantitatively converted to methyl pseudomonate C and pseudomonic acid C respectively with 80% acetic acid overnight.

EXAMPLE 12

Methyl pseudomonate C

Sodium iodide (600 mgs, 4 eq) (dried at 110° C./4 hours) was stirred in dry THF (1 ml) and dry acetonitrile (1 ml) and trifluoroacetic anhydride (141 μl, 1 eq) was added. After 5 minutes the yellow solution was cooled in ice and methyl pseudomonate A (514 mgs) added. After 5 minutes the ice bath was removed and the reaction stirred at room temperature for 24 hours. The reaction mixture was diluted with aqueous sodium bisulphite and extracted with ethyl acetate (4×25 ml). The combined extracts were washed with brine then dried (MgSO₄) and evaporated to an oil then chromatographed on silica (5 g). Pure fractions (tlc, hplc) were combined and evaporated to give desired product (63 mgs, 13%).

EXAMPLE 13

Isohexyl pseudomonate C

Methyl pseudomonate A (10 g) and potassium selenocyanate (4.32 g, 1.5 eq) in 2-ethyl-n-butanol (isohexyl alcohol)-water (9:1, 150 ml) were refluxed for 2 days. The solution was filtered and evaporated then the residue redissolved in ethyl acetate/water. The organic layer was separated, washed with brine then dried (MgSO₄) and the solvent removed in vacuo. The crude product was chromatographed on silica (100 g) eluting with 0 to 65% MeOH—CHCl₃. Fractions containing pure methyl pseudomonate C were combined and evaporated to an oil which crystallised on standing mp 47°–9° C. (2.2 g). Remaining fractions were combined and rechromatographed to yield a pure compound subsequently identified as isohexyl pseudomonate C (1.0 g) $v_{max}$ (CHCl$_3$) 3400 (broad), 1703, 1640, 1427, 1220, 1150, 1020 and 978 cm$^{-1}$, $\delta_H$ (CDCl$_3$) 0.94 (6H, t, (CH$_2$CH$_3$)$_2$), 0.97 (3H, d, C17-CH$_3$), 1.14 (3H, d, C14-CH$_3$), 1.32 (12H, m, —(CH$_2$)$_6$—), 2.19 (3H, s, C15-CH$_3$), 3.95 (2H, d, OCH$_2$CHEt$_2$), 4.05 (2H, t, C9'-CH$_2$), 5.45 (2H, m H-10, H-11) 5.75 (1H, s, H-2), $\delta_c$ (CDCl$_3$) 174.0 (C1'), 166.9 (C1), 157.2 (C3), 134.4, 129.0 (C10, C11), 117.8 (C2), 75.0 (C5), 71.2 (C13), 70.4 (C7), 68.8 (C6), 66.3 (OCH$_2$CHEt$_2$), 64.9 (C16), 63.8 (C9'), 44.4 (C12), 43.2 (C4), 42.1 (C8), 40.5 (OCH$_2$CHEt$_2$), 34.4 (C2'), 32.5 (C9), 29.1 (C4', C5', C6'), 28.8 (C8'), 26.0 (C7'), 25.0 (C3'), 23.4 (CH$_2$CH$_3$) 20.3 (C14), 19.2 (C15), 16.4 (C17), 11.0 (CH$_2$CH$_3$).

BIOLOGICAL DATA (1) Antibacterial activity - human organisms

Table 1 shows the antibacterial spectrum of sodium pseudomonate C and methyl pseudomonate C in terms of minimum inhibitory concentration (μg/ml) measured by serial dilution in nutrient agar containing 5% chocolated horse blood.

TABLE 1

| ORGANISM | M.I.C. (μg/ml) | |
|---|---|---|
| | sodium pseudomonate C | methyl pseudomonate C |
| E. coli NCTC 10418 | >100 | >100 |
| E. coli ESS | 1.0 | 2.5 |
| P. mirabilis 889 | >100 | >100 |
| K. aerogenes A | >100 | >100 |
| Ps aeruginosa NCTC 10701 | >100 | >100 |
| Pasteurella multocida 1633 | 1.0 | 2.5 |
| Haemophilus influenzae Q1 | 0.1 | <0.2 |
| Haeomophilus influenzae Wy 21 | 0.1 | 0.5 |
| Neisseria flavescens 6633 | 0.2 | 0.5 |
| Bacillus subtilis | 0.02 | <0.2 |
| Corynebacterium xerosis 9755 | >100 | >100 |
| Sarcina lutea | >100 | >100 |
| Staph. aureus Oxford | 0.1 | <0.2 |
| Staph. aureus Russell | 0.2 | 0.5 |
| Staph. aureus 1517 | 0.2 | 0.5 |
| Strep. faecalis I | 100 | >100 |
| Strep. Pyogenes A 64/848 | 0.1 | 1.0 |
| Strep. Pyogenes B 2788 | 2.5 | 1.0 |
| Strep. Pyogense C 2761 | 0.2 | 1.0 |
| Strep. pneumoniae CN33 | 0.1 | 0.1 |

(2) Anti-mycoplasma activity

Methyl pseudomonate C possess good antimycoplasma activity in vitro against mycoplasmas from human and veterinary sources, as shown in table 2.

Method (1) The minimum inhibitory concentrations (MIC) of methyl pseudomonate C were determined in Microtitre plates, by a modification of the metabolic-inhibition test (Taylor-Robinson, 1967). The compounds were serially diluted in sterile de-ionised water to give a range of concentrations from 250-0.5 μg/ml. Mycoplasma broth containing 1% (w/v) of glucose and 0.005% (w/v) of phenon red, was added at a strength to compensate for its dilution by the aqueous drug solution. Approximately 10$^4$ colony forming units of mycoplasma were added to each concentration of drug. Drug-free infected, non-infected and pH control wells were included on each plate. Plates were sealed with cellophane tape and incubated at 37° C. for seven days. The MIC was the lowest concentration of compound that prevented a colour change in the mycoplasma broth, caused by the metabolism.

Reference

Taylor-Robinson, 1967. Mycoplasmas of various hosts and their antibiotic sensitivities. Post. Grad. Med. J., 43 Suppl. [March], 100.

TABLE 2

| MYCOPLASMA | M.I.C. (μg/ml) |
|---|---|
| M. gallisepticum S.6 | 62.5 |
| M. synoviae 25204 | <0.5 |
| M. pulmonis JB | <0.5 |
| M. suipneumoniae Laber | <0.5 |
| M. pneumoniae 427a | 1.0 |
| M. fermentans MW KL4 | <0.5 |

Table 3 shows MIC values for sodium pseudomonate C and methyl pseudomonate C against further mycoplasma species determined in Friis' broth using the microtiter method.

TABLE 3

| ORGANISM | M.I. C. (μg/ml) | |
|---|---|---|
| | Methyl Pseudomonate C | Sodium Pseudomonate C |
| M. suipneumoniae Str. 11 | >10 | >10 |
| M. suipneumoniae J2206/183b | >10 | 10 |
| M. dispar H225 | 10 | 5.0 |
| M. dispar NCTC 10125 | 50 | 2.5 |
| M. pneumoniae 427a | >10 | 2.5 |
| M. pneumoniae ATCC 15492 | 10 | — |
| M. fermentans MWKL4 | 0.039 | <0.02 |
| M. pulmonis JB | 0.312 | 0.039 |

We claim:

1. A compound selected from the group consisting of an acid of formula:

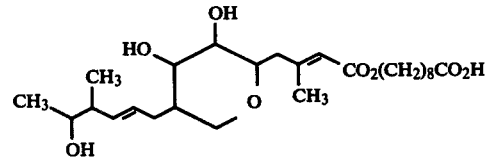

or a pharmaceutically acceptable salt or ester thereof.

2. A compound according to claim 1 which is the acid therein depicted, an alkali metal salt thereof or an alkyl ester wherein the alkyl group has from 1 to 6 carbon atoms thereof.

3. Pseudomonic acid C.
4. Sodium pseudomonate C.
5. Methyl pseudomonate C.
6. iso-Hexyl pseudomonate C.

* * * * *